(12) United States Patent
Chen et al.

(10) Patent No.: US 12,559,727 B2
(45) Date of Patent: Feb. 24, 2026

(54) INDUCER FOR INDUCING DIFFERENTIATION OF MESENCHYMAL STEM CELLS INTO ESTRADIOL-SECRETING CELLS

(71) Applicant: Qingdao Ruiside Biological Technology Co., Ltd., Qingdao (CN)

(72) Inventors: Mengmeng Chen, Qingdao (CN); Bingqiang Zhang, Qingdao (CN)

(73) Assignee: Qingdao Ruiside Biological Technology Co., Ltd., Qingdao (CN)

( * ) Notice: Subject to any disclaimer, the term of this patent is extended or adjusted under 35 U.S.C. 154(b) by 0 days.

(21) Appl. No.: 18/260,247

(22) PCT Filed: Jan. 4, 2023

(86) PCT No.: PCT/CN2023/070348
§ 371 (c)(1),
(2) Date: Jul. 2, 2023

(87) PCT Pub. No.: WO2023/226441
PCT Pub. Date: Nov. 30, 2023

(65) Prior Publication Data
US 2025/0092367 A1      Mar. 20, 2025

(30) Foreign Application Priority Data
May 26, 2022    (CN) .......................... 202210579694.3

(51) Int. Cl.
*C12N 5/071* (2010.01)
*C12N 5/00* (2006.01)

(52) U.S. Cl.
CPC ......... *C12N 5/0682* (2013.01); *C12N 5/0037* (2013.01); *C12N 2500/38* (2013.01); *C12N 2500/46* (2013.01); *C12N 2501/14* (2013.01); *C12N 2501/155* (2013.01); *C12N 2501/165* (2013.01); *C12N 2501/999* (2013.01); *C12N 2506/1346* (2013.01)

(58) Field of Classification Search
CPC ............................ C12N 5/0682; C12N 5/0037; C12N 2501/14; C12N 2501/155; C12N 2501/165; C12N 2506/1346; C12N 2506/1384
See application file for complete search history.

(56) References Cited

U.S. PATENT DOCUMENTS

2017/0258842 A1    9/2017  Al-Hendy
2018/0221419 A1    8/2018  Atwood et al.

FOREIGN PATENT DOCUMENTS

CN        104293873 A    1/2015
CN        106929466 A    7/2017

OTHER PUBLICATIONS

Nakamura (Physiol. Plant. 36: 293-296. 1976).*
Di Man,et al. Modeling of induction of placental mesenchymal stem cells of rats differentiating into endometrial epithelial cells in vitro by simulated uterine microenvironment, Chin J Fam Plann, Nov. 30, 2021 (Nov. 30, 2021) [Unable to acquire the document].
Maghami RG, et al. "Differentiation of mesenchymal stem cells to germ-like cells under induction of Sertoli cell-conditioned medium and retinoic acid", Andrologia, Sep. 25, 2017 (Sep. 25, 2017) [Unable to acquire the document].
International search report of PCT/CN2023/070348.

* cited by examiner

*Primary Examiner* — Valarie E Bertoglio
(74) *Attorney, Agent, or Firm* — Hemisphere Law, PLLC

(57) ABSTRACT

The present disclosure belongs to the field of biological medicines, and relates to an inducer for inducing differentiation of mesenchymal stem cells into estradiol-secreting cells. The inducer for inducing differentiation of mesenchymal stem cells into estradiol-secreting cells uses human mesenchymal stem cell serum-free culture medium as a substrate and comprises the following components in mass concentration ratios: 20-60 mg/L of bone morphogenetic protein-4, 20-60 mg/L of bone morphogenetic protein-7, 2-8 mg/L of retinoic acid, 2-8 mg/L of resveratrol, 2-8 mg/L of icariin, 2-8 μg/L of benzamide, 2-8 μg/L of chloroplatinic acid hexahydrate, 2-8 μg/L of ethanolamine, 2-10 μg/L of erythropoietin and 2-10 μg/L of vascular endothelial growth factor. The inducer for inducing differentiation of mesenchymal stem cells into estradiol-secreting cells provided by the present disclosure has a high induction efficiency.

2 Claims, No Drawings

INDUCER FOR INDUCING DIFFERENTIATION OF MESENCHYMAL STEM CELLS INTO ESTRADIOL-SECRETING CELLS

TECHNICAL FIELD

The present disclosure belongs to the field of biological medicines, and relates to an inducer for inducing differentiation of mesenchymal stem cells into estradiol-secreting cells.

BACKGROUND

Estrogen plays an important role in women's lives, which cannot be replaced by any hormones. It dominates the development and maintenance of women's secondary sex characteristic, regulates the stability of women's internal environment, controls women's life cycle, and women's periodic menstruation, women's fertility, women's unique plump posture and the like are inseparable from the role of estrogen. There are three main estrogens that exist physiologically in a human body, including estradiol (E2), estrone and estriol, which are mainly generated by ovaries, follicles, corpus luteum and gestational placenta, and the lack of estrogen will cause the hypofunction of multiple organs of women's body.

Premature ovarian failure (POF) refers to a phenomenon of amenorrhea before 40 years old caused by ovarian function failure. It is characterized in that primary or secondary amenorrhea is accompanied by an increase in blood gonadotropin levels and a decrease in estrogen levels, and is accompanied by a series of low estrogen symptoms to varying degrees, such as hot flashes and sweats, red cheeks, and low sexual desire. Now for POF women, hormone replacement therapy is generally adopted to improve various complications caused by low estrogen level, exogenous steroid hormone is given to POF patients for artificial cycle, so that endometrim is normally developed, and pregnancy is facilitated. However, sine long-term hormone replacement therapy difficultly achieves rational dosage, it is possible to have adverse effects and potential risk to cause low ovarian function recovery efficiency. Thus, it is urgent to seek another way to address this problem.

Germ cells (PGCs) are a generic term of cells in multicellular organisms capable of propagating progenies, from primitive germ cells to finally differentiated germ cells, including sperms and egg cells. At the later stage of embryo development, the germ cells are no longer divided and proliferated. Only a small part of oogoniums grow and are differentiated into primary oocytes. After a series of processes, the primary oocytes form primordial follicles, then enter into growing follicles through preantral follicles, and finally form mature follicles. After a woman is born, the number of oocytes continues to decrease. When the number of oocytes decreases to a certain extent, it can lead to menopause. At the same time, menopause is accompanied by a decrease in estrogen content. The decrease in estrogen can also lead to various diseases in women, such as cardiovascular, cerebrovascular, endocrine, bone, and nervous systems.

In the process of differentiation of stem cells into functional oocyte like cells, the synthesis of sex hormones (such as estrogen and androgen) is inevitable due to the simultaneous development of newly generated follicles. At the same time, sex hormones act on oocytes to promote their development. Due to the production of androgens by follicular membrane cells, androgens are transported to granulosa cells and then estrogen is produced. Under the regulation of the patient's own hypothalamic pituitary anterior lobe target gland axis, the hormone required for physiological activities of the body is supplemented through feedback and negative feedback mechanisms, thereby avoiding the problem of excessive or insufficient supplementation caused by hormone replacement therapy. This is different from traditional exogenous hormone supplementation and its biggest advantage. The current methods of inducing stem cells mainly include in vitro induction, gene modification, protein transduction, and tissue microenvironment induction, wherein in vitro induction uses combinations of different stimulating factors to induce differentiation of stem cells into target cells. The conditions for inducing differentiation vary in each laboratory, and a mechanism for inducing differentiation is still unclear. The in vitro induction has the disadvantages of low induction efficiency, complicated induction process, long induction time, a small number of resulting cells and low function.

At present, many studies have focused on the preparation of embryoid bodies from mesenchymal stem cells and co-culture with follicular fluid and Leukemia inhibitory factor (LIF). Professor Songyangzhou of Sun Yat-sen University used retinoic acid (RA) as an inducer to induce differentiation of embryonic stem cells into germ cells. Previously, it was also reported that RA induced differentiation of umbilical cord stem cells into PCGs. However, only one article reported that RA could induce differentiation of stem cells into germ cell or promote stem cells to secrete E2 and other estrogens, and a differentiation rate was not significantly different from that in blank group.

Bone morphogenetic proteins (BMPs) are important regulators regulating the production of estrogen and progestogen, which can improve the responsiveness of granulosa cells to follicle estrogen, promote the production of E2, and inhibit the production of progesterone. It is found that bone morphogenetic protein-4 (BMP4) and bone morphogenetic protein-7 (BMP7) can inhibit the secretion of progesterone and increase the secretion of E2 through a paracrine signaling effect. Its mechanism of action may promote the transformation of primordial follicles to primary follicles. Kehkooi Kee and Katsuhiko, et al. have published similar papers in journals such as Nature and Science, using BMP4, BMP7, and BMP8b as inducers to induce differentiation of embryonic stem cells into PGCs.

Based on the above considerations, the present disclosure is attempted to seek a high-efficiency inducer for differentiating mesenchymal stem cells into E2-secreting cells by combining the inducer for differentiating embryonic stem cells into germ cells and the inducer for differentiating mesenchymal stem cells into germ cells. Based on the literature and repeated tests, the inventor found that on the basis of BMP4, BMP7 and RA in combination with benzamide, bhloroplatinic acid hexahydrate and ethanolamine, the efficiency of inducing the differentiation of mesenchymal stem cells into E2-secreting cells can be significantly improved, while the combination of antioxidant resveratrol, icariin, and growth factor erythropoietin (EPO) and vascular endothelial growth factor (VEGF) can significantly increase the survival rate and value-added ability of E2-secreting cells obtained after induction.

SUMMARY

The objective of the present disclosure is to address the above problems existing in the prior art to provide an inducer for inducing differentiation of mesenchymal stem cells into estradiol (E2)-secreting cells. The inducer uses human mesenchymal stem cell serum-free culture medium as a substrate and comprises the following components in mass concentration ratios: 20-60 mg/L of bone morphogenetic protein-4 (BMP4), 20-60 mg/L of bone morphogenetic protein-7 (BMP7), 2-8 mg/L of retinoic acid (RA), 2-8 mg/L of resveratrol, 2-8 mg/L of icariin, 2-8 µg/L of benzamide, 2-8 µg/L of chloroplatinic acid hexahydrate, 2-8 µg/L of ethanolamine, 2-10 µg/L of erythropoietin (EPO) and 2-10 µg/L of vascular endothelial growth factor (VEGF). The inducer of the present disclosure has less steps and short time required for inducing differentiation, with a high induction efficiency.

To achieve the above objective, the technical solution adopted by the present disclosure is as follows: an inducer for inducing differentiation of mesenchymal stem cells into E2-secreting cells comprises the following components: BMP4, BMP7, RA, resveratrol, icariin, benzamide, chloroplatinic acid hexahydrate, ethanolamine, EPO and VEGF.

The inducer comprises the following components in mass concentration ratios: 20-60 mg/L of BMP4, 20-60 mg/L of BMP7, 2-8 mg/L of RA, 2-8 mg/L of resveratrol, 2-8 mg/L of icariin, 2-8 µg/L of benzamide, 2-8 µg/L of chloroplatinic acid hexahydrate, 2-8 µg/L of ethanolamine, 2-10 µg/L of EPO and 2-10 µg/L of VEGF.

Preferably, the inducer comprises the following components in mass concentration ratios: 50 mg/L of BMP4, 50 mg/L of BMP7, 8 mg/L of RA, 6 mg/L of resveratrol, 6 mg/L of icariin, 4 µg/L of benzamide, 6 µg/L of chloroplatinic acid hexahydrate, 4 µg/L of ethanolamine, 5 µg/L of EPO and 5 µg/L of VEGF.

The inducer for inducing differentiation of mesenchymal stem cells into E2-secreting cells provided by the present disclosure has the following advantages: 1, there are no genetic change or cancer risk due to no genetic transfection, with high safety; 2, less induction steps and short induction time; 3, the combination of benzamide, chloroplatinic acid hexahydrate and ethanolamine can greatly improve the efficiency of inducing differentiation of mesenchymal stem cells into E2-secreting cells; 4, the combination of antioxidants resveratrol, icariin, and growth factors EPO and VEGF can significantly enhance the viability and value-added ability of E2-secreting cells obtained after induction.

DETAILED DESCRIPTION OF THE EMBODIMENTS

Unless specially stated, experimental methods in the following examples are all conventional methods. Instruments and reagents used in the experiment are commercially available.

Example 1

An inducer for inducing differentiation of mesenchymal stem cells into E2-secreting cells in this example comprised the following components in mass concentration ratios: 40 mg/L of BMP4, 50 mg/L of BMP7, 8 mg/L of RA, 2 mg/L of resveratrol, 6 mg/L of icariin, 4 µg/L of benzamide, 8 µg/L of chloroplatinic acid hexahydrate, 4 µg/L of ethanolamine, 10 µg/L of EPO and 2 µg/L of VEGF. The above components were successively added into a human mesenchymal stem cell serum-free culture medium (or DMEM+10% FBS or other types of commercially available mesenchymal stem cell culture mediums) in the mass concentration ratios, evenly mixed and filtered to remove bacteria.

The various components of the inducer of the present disclosure were all commercially available products: a human mesenchymal stem cell serum-free culture medium with brand LONZA, and article number 00190632; BMP4 with brand Gibco, and article number PHC9533; BMP7 with brand Gibco, and article number PHC7204; RA with brand Sigma, and article number R2625; resveratrol with brand Sigma, and article number R5010-100 MG; icariin with brand Shanghai Microcrystalline Biology, and articule number 489-32-7; benzamide with brand Sigma, and article number 135828; chloroplatinic acid hexahydrate with brand Sigma, and article number 206083; ethanolamine with brand Sigma, and article number 8008490100; EPO with brand PeproTech, and article number CYT-201; VEGF with brand PeproTech, and article number 96-100-20-2.

Example 2

An inducer for inducing differentiation of mesenchymal stem cells into E2-secreting cells in this example comprised the following components in mass concentration ratios: 50 mg/L of BMP4, 20 mg/L of BMP7, 2 mg/L of RA, 2 mg/L of resveratrol, 2 mg/L of icariin, 4 µg/L of benzamide, 6 µg/L of chloroplatinic acid hexahydrate, 4 µg/L of ethanolamine, 8 µg/L of EPO and 8 µg/L of VEGF. The above components were successively added into a human mesenchymal stem cell serum-free culture medium (or DMEM+10% FBS or other types of commercially available mesenchymal stem cell culture mediums) in the mass concentration ratios, evenly mixed and filtered to remove bacteria.

Example 3

An inducer for inducing differentiation of mesenchymal stem cells into E2-secreting cells in this example comprised the following components in mass concentration ratios: 50 mg/L of BMP4, 50 mg/L of BMP7, 8 mg/L of RA, 6 mg/L of resveratrol, 6 mg/L of icariin, 4 µg/L of benzamide, 6 µg/L of chloroplatinic acid hexahydrate, 4 µg/L of ethanolamine, 5 µg/L of EPO and 5 µg/L of VEGF. The above components were successively added into a human mesenchymal stem cell serum-free culture medium (or DMEM+10% FBS) in the mass concentration ratios, evenly mixed and filtered to remove bacteria.

Example 4

By example of human adipose mesenchymal stem cells, the effect of the inducer of the present disclosure on inducing differentiation of mesenchymal stem cells into E2-secreting cells was illustrated. The 3 generations of human adipose mesenchymal stem cells were passaged and inoculated into a 96-well plate in an amount of $1\times10^4/cm^2$. When almost 80% of cells were fused and vigorously gre, differentiation was induced. The induction conditions are seen in Table 1.

TABLE 1

| Induction condition groups | |
|---|---|
| Group | Inducer |
| Control group (blank) | Human mesenchymal stem cells serum-free culture medium (no inducer) |
| Induction group 1 | Human mesenchymal stem cells serum-free culture medium + BMBP4 50 mg/L + BMP7 50 mg/L |
| Induction group 2 | Human mesenchymal stem cells serum-free culture medium + BMBP4 50 mg/L + BMP7 50 mg/L + RA 8 mg/L |
| Induction group 3 | Human mesenchymal stem cells serum-free culture medium + BMBP4 50 mg/L + BMP7 50 mg/L + RA 8 mg/L + resveratrol 6 mg/L + icariin 6 mg/L |
| Induction group 4 | Human mesenchymal stem cells serum-free culture medium + BMBP4 50 mg/L + BMP7 50 mg/L + RA 8 mg/L + resveratrol 6 mg/L + icariin 6 mg/L + benzamide 4 µg/L |
| Induction group 5 | Human mesenchymal stem cells serum-free culture medium + BMBP4 50 mg/L + BMP7 50 mg/L + RA 8 mg/L + resveratrol 6 mg/L + icariin 6 mg/L + benzamide 4 µg/L + chloroplatinic acid hexahydrate 6 µg/L |
| Induction group 6 | Human mesenchymal stem cells serum-free culture medium + BMBP4 50 mg/L + BMP7 50 mg/L + RA 8 mg/L + resveratrol 6 mg/L + icariin 6 mg/L + benzamide 4 µg/L + chloroplatinic acid hexahydrate 6 µg/L + ethanolamine 4 µg/L |
| Induction group 7 (present disclosure) | Human mesenchymal stem cells serum-free culture medium + BMBP4 50 mg/L + BMP7 50 mg/L + RA 8 mg/L + resveratrol 6 mg/L + icariin 6 mg/L + benzamide 4 µg/L + chloroplatinic acid hexahydrate 6 µg/L + ethanolamine 4 µg/L + EPO 5 µg/L + VEGF 5 µg/L |

The morphological change of cells during the induction was carefully observed. At the induction time of 1-9 days, a culture solution was taken from each group and then centrifuged at 2000r/min for 10 min, and the supernatant was stored at −20° C., subsequently the E2 content was respectively detected and statistically analyzed. The E2 content was detected following operations specified by the instruction of an estradiol ELISA kit (Shanghai Ongke Biotechnology Co., Ltd). The results are seen in Table 2.

TABLE 2

Comparison of induction results of different inducers.

| Group | After 1 day | After 2 day | After 3 day | After 4 day | After 5 day | After 6 day | After 7 day | After 8 day | After 9 day |
|---|---|---|---|---|---|---|---|---|---|
| | E2 secretion (pg/ml)(n = 5, $\bar{x} \pm s$) | | | | | | | | |
| Control group | 3.1 ± 0.3 | 3.4 ± 0.1 | 2.9 ± 0.2 | 3.4 ± 0.1 | 4.1 ± 0.2 | 5.1 ± 0.3 | 5.2 ± 0.3 | 5.5 ± 0.1 | 5.6 ± 0.1 |
| Induction group 1 | 25.2 ± 1.0 | 43.8 ± 1.4 | 52.6 ± 2.7 | 61.6 ± 3.6 | 71.6 ± 4.6 | 79.2 ± 4.4 | 91.6 ± 3.7 | 89.6 ± 1.9 | 94.6 ± 4.6 |
| Induction group 2 | 27.8 ± 1.5 | 47.5 ± 2.1 | 97.4 ± 3.3 | 117.9 ± 22.0 | 127.3 ± 12.5 | 163.6 ± 13.7 | 187.4 ± 9.2 | 259.5 ± 213 | 280.0 ± 12.9 |
| Induction group 3 | 44.0 ± 2.3 | 96.9 ± 11.5 | 144.5 ± 7.8 | 189.8 ± 7.6 | 260.0 ± 1.7 | 365.5 ± 11.0 | 374.3 ± 23.4 | 477.7 ± 22.1 | 510.3 ± 11.9 |
| Induction group 4 | 46.8 ± 2.4 | 123.3 ± 9.7 | 189.9 ± 23.4 | 288.0 ± 22.9 | 349.1 ± 9.3 | 469.3 ± 18.5 | 533.3 ± 32.6 | 627.7 ± 21.7 | 680.4 ± 23.5 |
| Induction group 5 | 55.7 ± 9.4 | 123.9 ± 14.6 | 207.4 ± 12.5 | 326.0 ± 21.8 | 425.9 ± 21.1 | 530.4 ± 29.7 | 617.7 ± 28.4 | 719.3 ± 24.5 | 813.4 ± 17.8 |
| Induction group 6 | 83.2 ± 2.6 | 132.2 ± 13.2 | 217.2 ± 21.1 | 319.2 ± 17.0 | 432.2 ± 18.9 | 632.2 ± 23.8 | 791.2 ± 19.6 | 823.2 ± 32.3 | 932.2 ± 28.5 |
| Induction group 7 | 87.2 ± 2.5 | 196.2 ± 11.5 | 278.2 ± 12.7 | 387.2 ± 13.8 | 513.2 ± 22.1 | 687.2 ± 21.9 | 878.2 ± 19.6 | 941.2 ± 27.5 | 1187.2 ± 32.8 |

It can be seen from the induction results in Table 2 that the induction of human adipose mesenchymal stem cells using the inducer of the present disclosure has the highest efficiency, and the cells obtained by induction secrete the most content of E2. After the inducer of the present disclosure is added, E2 is continuously secreted after 2 days, and the secretion gradually increases. The maximum daily secretion of E2 can be reached about 5-7 days after induction, and E2 can be continuously secreted.

What is claimed is:

1. An inducer for inducing differentiation of mesenchymal stem cells into estradiol-secreting cells, wherein the inducer comprises the following components in mass concentration ratios: 20-60 mg/L of bone morphogenetic protein-4, 20-60 mg/L of bone morphogenetic protein-7, 2-8 mg/L of retinoic acid, 2-8 mg/L of resveratrol, 2-8 mg/L of icariin, 2-8 ug/L of benzamide, 2-8 ug/L of chloroplatinic acid hexahydrate, 2-8 ug/L of ethanolamine, 2-10 ug/L of erythropoietin and 2-10 ug/L of vascular endothelial growth factor.

2. The inducer for inducing differentiation of mesenchymal stem cells into estradiol-secreting cells according to claim 1, wherein the inducer comprises the components in the following mass concentration ratios: 50 mg/L of bone morphogenetic protein-4, 50 mg/L of bone morphogenetic protein-7, 8 mg/L of retinoic acid, 6 mg/L of resveratrol, 6 mg/L of icariin, 4 ug/L of benzamide, 6 ug/L of chloroplatinic acid hexahydrate, 4 ug/L of ethanolamine, 5 ug/L of erythropoietin and 5 ug/L of vascular endothelial growth factor.

* * * * *